United States Patent
Dang et al.

(10) Patent No.: US 9,643,943 B2
(45) Date of Patent: May 9, 2017

(54) PROCESS FOR FORMING PROPYLENE OXIDE FROM OXIDATION OF METHYL BENZYL ALCOHOL

(71) Applicant: Lyondell Chemical Technology, L.P., Houston, TX (US)

(72) Inventors: Vu A. Dang, Bear, DE (US); David W. Leyshon, Houston, TX (US); Sandor Nagy, Seabrook, TX (US); Roger A. Grey, West Chester, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/093,370

(22) Filed: Apr. 7, 2016

(65) Prior Publication Data

US 2016/0297783 A1    Oct. 13, 2016

Related U.S. Application Data

(60) Provisional application No. 62/145,308, filed on Apr. 9, 2015.

(51) Int. Cl.

| | | |
|---|---|---|
| *C07D 301/12* | (2006.01) | |
| *C07D 303/04* | (2006.01) | |
| *B01J 29/70* | (2006.01) | |
| *C07D 301/32* | (2006.01) | |
| *C07D 301/36* | (2006.01) | |

(52) U.S. Cl.
CPC ........ *C07D 301/12* (2013.01); *B01J 29/7088* (2013.01); *C07D 301/32* (2013.01); *C07D 301/36* (2013.01); *C07D 303/04* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,897,085 A | 1/1990 | Cochran et al. |
| 4,897,252 A | 1/1990 | Cochran et al. |
| 4,975,266 A | 12/1990 | Albal et al. |
| 4,996,374 A | 2/1991 | Lin et al. |
| 5,039,508 A | 8/1991 | Cochran et al. |
| 5,254,326 A | 10/1993 | Leyshon et al. |
| 8,124,555 B2 | 2/2012 | Mandimutsira et al. |
| 8,440,846 B2 | 5/2013 | Dang et al. |
| 8,703,983 B2 | 4/2014 | Crampton |
| 2004/0249176 A1 | 12/2004 | Strickler et al. |
| 2011/0190518 A1 | 8/2011 | Wolff et al. |
| 2016/0185741 A1 | 6/2016 | Teles et al. |

FOREIGN PATENT DOCUMENTS

| | | | |
|---|---|---|---|
| DE | WO 03050100 A1 * | 6/2003 | ............ B01J 19/006 |
| JP | 2011111431 A | 6/2011 | |
| WO | WO-03050100 A1 | 6/2003 | |
| WO | WO-2011119217 A1 | 9/2011 | |
| WO | WO-2015010992 A1 | 1/2015 | |

OTHER PUBLICATIONS

L. Sümegi et al., On the Mechanism of Propylene Epoxidation Catalyzed by Molybdenum Naphthenate, Reaction Kinetics and Catalysis Letters, vol. 12, No. 1, Mar. 1979, pp. 57-62, XP055042339, ISSN: 0133-1736, DOI: 10.1007/BF02071425.
PCT/US2016/026468 International Search Report and Written Opinion Mailed Jun. 8, 2016.

\* cited by examiner

*Primary Examiner* — Heidi Reese

(57) ABSTRACT

The present disclosure relates to a method of preparing propylene oxide comprising the steps:
(a) oxidizing alpha-methylbenzyl alcohol with air to form a first reaction mixture comprising hydrogen peroxide and acetophenone;
(b) reacting propylene with the first reaction mixture in the presence of a catalyst to form a second reaction mixture comprising propylene oxide;
(c) separating the propylene oxide from the second reaction mixture to form a third reaction mixture;
(d) heating the third reaction mixture to decompose hydrogen peroxide, whereby a fourth reaction mixture is formed;
(e) hydrogenating the acetophenone in the fourth reaction mixture with hydrogen to form a fifth reaction mixture comprising alpha-methylbenzyl alcohol; and
(f) separating alpha-methylbenzyl alcohol from the fifth reaction mixture and returning the methyl benzyl alcohol to step (a).

20 Claims, 3 Drawing Sheets

PROCESS FOR FORMING PROPYLENE OXIDE FROM OXIDATION OF METHYL BENZYL ALCOHOL

CROSS-REFERENCE TO RELATED APPLICATIONS

This application claims the benefit of priority to U.S. Provisional Application No. 62/145,308, filed on Apr. 9, 2015, which is incorporated herein by reference in its entirety.

BACKGROUND OF THE INVENTION

I. Technical Field

The present disclosure relates to new methods for the epoxidation of olefins.

II. Description of Related Art

Propylene oxide is a colorless volatile liquid and is produced on a large scale industrially. Its major application includes the production of polyether polyols for use in making polyurethane plastics. Generally, there are three major commercial processes employed for the production of propylene oxide. One process is based on chlorohydrin technology (Scheme 1). Another utilizes the epoxidation of propylene with hydroperoxides. The third uses hydrogen peroxide to epoxidize propylene.

Scheme 1. Chlorohydrin process to propylene oxide

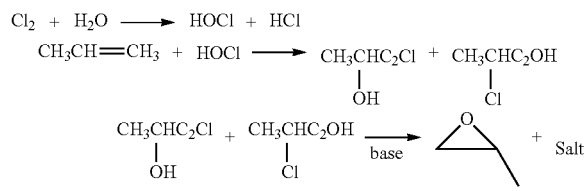

Hydroperoxide epoxidation of propylene requires an air oxidation of ethyl benzene or isobutane in a separate prior step to produce ethylbenzene hydroperoxide or tert-butyl-hydroperoxide, respectively, which is then reacted with propylene in the presence of a catalyst (such as soluble molybdenum supported titanium) to produce propylene oxide and the co-products alpha-methyl benzyl alcohol (1-ethylphenyl alcohol or MBA) and t-butyl alcohol, respectively (Scheme 2).

Scheme 2. Hydroperoxide epoxidation of propylene

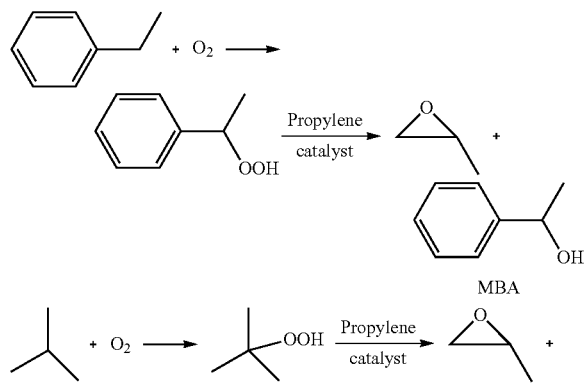

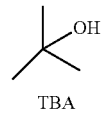

The oxidation of propylene via cumene hydroperoxide was commercialized by Sumitomo Chemical. This process is also in the hydroperoxide class. Cumene hydroperoxide is pre-formed in a separate step (autoxidation of cumene), which is the same as ethylbenezene and isobutene oxidation described above, except in this case the coproduct cumyl alcohol produced from the epoxidation is converted back to cumene via hydrogenolysis.

Scheme 3. Cumene PO process

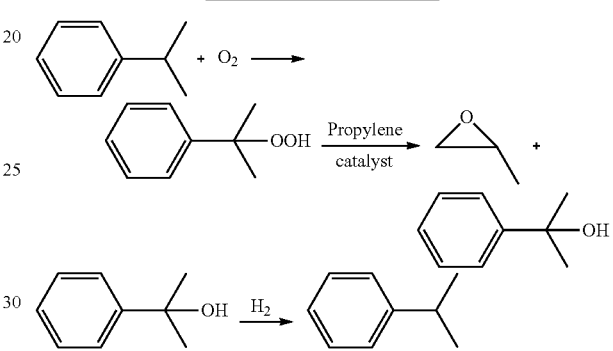

Utilizing hydrogen peroxide, BASF and Dow Chemical developed a process to produce propylene oxide by oxidizing propylene with aqueous hydrogen peroxide in methanol solution using titanium silicate catalysts (TS1) in 2009.

In the 1990's a process for the production of $H_2O_2$ via alpha-methylbenzyl alcohol (1-phenylethyl alcohol or MBA) oxidation, which involved the formation of acetophenone as a co-product, was developed by Lyondell Chemical Company. At that time there were no good catalysts for the epoxidation of propylene with hydrogen peroxide. Later, TS1 was shown to be an efficient catalyst for the epoxidation of propylene using $H_2O_2$, but it requires a methanol solvent to be effective. Since methanol is a small molecule, it will react with propylene oxide to yield undesirable ring opening byproducts such as 1-methoxy-2-propanol or 2-methoxy-1-propanol. In addition, water, which is also used as a cosolvent in most cases, will also react with propylene oxide to yield propylene glycol as a byproduct. In both situations, propylene oxide yield will be reduced because of the ring opening side reactions taken place.

SUMMARY OF THE INVENTION

In one aspect of the present disclosure, there are provided methods of preparing propylene oxide comprising:
(a) oxidizing alpha-methylbenzyl alcohol with air to form a first reaction mixture comprising hydrogen peroxide and acetophenone;
(b) reacting propylene with the first reaction mixture in the presence of a catalyst to form a second reaction mixture comprising propylene oxide;
(c) separating the propylene oxide from the second reaction mixture to form a third reaction mixture;

(d) heating the third reaction mixture to decompose hydrogen peroxide, whereby a fourth reaction mixture is formed;
(e) hydrogenating the acetophenone in the fourth reaction mixture with hydrogen to form a fifth reaction mixture comprising alpha-methylbenzyl alcohol; and
(f) separating alpha-methylbenzyl alcohol from the fifth reaction mixture and returning the alpha-methylbenzyl alcohol to step (a).

In some embodiments, the molar ratio of the alpha-methylbenzyl alcohol to the oxygen of the air of step (a) is from 1:1 to 10:1. In some embodiments, the oxidizing reaction of step (a) is conducted at a temperature from 100° C. to 160° C. In some embodiments, the catalyst is a titanium support on zeolite catalyst. In some embodiments, the titanium support on zeolite catalyst is a TiMWW catalyst or a layered TiMWW catalyst. In some embodiments, the molar ratio of propylene to hydrogen peroxide in step (b) is from 3:1 to 10:1. In some embodiments, step (b) is conducted at a temperature from 20° C. to 150° C. In some embodiments, step (b) is conducted at a pressure from 80 psig (653 kPa) to 800 psig (5,617 kPa). In some embodiments, step (b) further comprises a solvent. In some embodiments, the solvent is alpha-methylbenzyl alcohol and acetophenone or t-butyl alcohol. In some embodiments, step (b) comprises a weight ratio of alcohol to ketone to hydrogen peroxide to water from 96:1:2.9:0.1 to 44:44:11.7:0.3. In some embodiments, step (b) further comprises conducting the epoxidation reaction in the presence of a buffer. In some embodiments, the buffer is ammonium acetate, ammonium phosphate, or ammonium dihydrogen phosphate. In some embodiments, the separation of step (c) comprises distilling the propylene oxide from the second reaction mixture. In some embodiments, the distillation is conducted at a temperature from 40° C. to 170° C. In some embodiments, step (d) is conducted at a temperature from 150° C. to 200° C. In some embodiments, the molar ratio of the acetophenone to hydrogen in step (e) is from 1:4 to 10:1. In some embodiments, step (e) is conducted at a temperature from 60° C. to 100° C. In some embodiments, step (e) is conducted at a pressure from 250 psig (1,825 kPa) to 500 psig (3,548 kPa). In some embodiments, the separation of step (f) comprises distilling the alpha-methylbenzyl alcohol from the fifth reaction mixture. In some embodiments, the distillation is conducted at a temperature from 50° C. to 150° C. In some embodiments, the method further comprises washing the fifth reaction mixture with a base. In some embodiments, the base is an aqueous solution of sodium hydroxide or potassium hydroxide with a concentration from 0.1 wt. % to 25 wt. %. In some embodiments, the method further comprises reacting the fifth reaction mixture after the separation of alpha-methyl benzyl alcohol with hydrogen in the presence of a hydrogenation catalyst forming a sixth reaction mixture and returning at least the alpha-methylbenzyl alcohol from the sixth reaction mixture to step (a).

Other objects, features and advantages of the present disclosure will become apparent from the following detailed description. It should be understood, however, that the detailed description and the specific examples, while indicating specific embodiments, are given by way of illustration only, since various changes and modifications within the spirit and scope of the appended claims will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. The embodiments provided herein may be better understood by reference to one of these drawings in combination with the detailed description.

DETAILED DESCRIPTION OF THE INVENTION

In some aspects, the present disclosure provides processes for preparing epoxides that comprise oxidizing olefins using an oxidizing agent that is produced by the oxidation of an alcohol with air, whereby the alcohol is regenerated and then reused in a reaction loop. In one aspect of the present disclosure, there are provided methods of preparing propylene oxide comprising:
(a) oxidizing alpha-methylbenzyl alcohol with air to form a first reaction mixture comprising hydrogen peroxide and acetophenone;
(b) reacting propylene with the first reaction mixture in the presence of a catalyst to form a second reaction mixture comprising propylene oxide;
(c) separating the propylene oxide from the second reaction mixture to form a third reaction mixture;
(d) heating the third reaction mixture to decompose hydrogen peroxide, whereby a fourth reaction mixture is formed;
(e) hydrogenating the acetophenone in the fourth reaction mixture with hydrogen to form a fifth reaction mixture comprising alpha-methylbenzyl alcohol; and
(f) separating alpha-methylbenzyl alcohol from the fifth reaction mixture and returning the alpha-methylbenzyl alcohol to step (a).

In some aspects, the present disclosure relates to one or more of the steps described herein. In some embodiments, each of the steps may be taken individually or the steps may be taken together to form a complete process. Furthermore, in some embodiments, the methods provided herein may further comprise one or more additional steps such as washing the fifth reaction mixture with a base or reacting the fifth reaction mixture after the separation of the alpha-methylbenzyl alcohol with hydrogen and a hydrogenation catalyst forming a sixth reaction mixture to decompose other by-products such as bis-alpha-methylbenzyl ethers to form more alpha-methylbenzyl alcohol. In some embodiments, the sixth reaction mixture is returned to the reaction of step (a).

Figure 1:
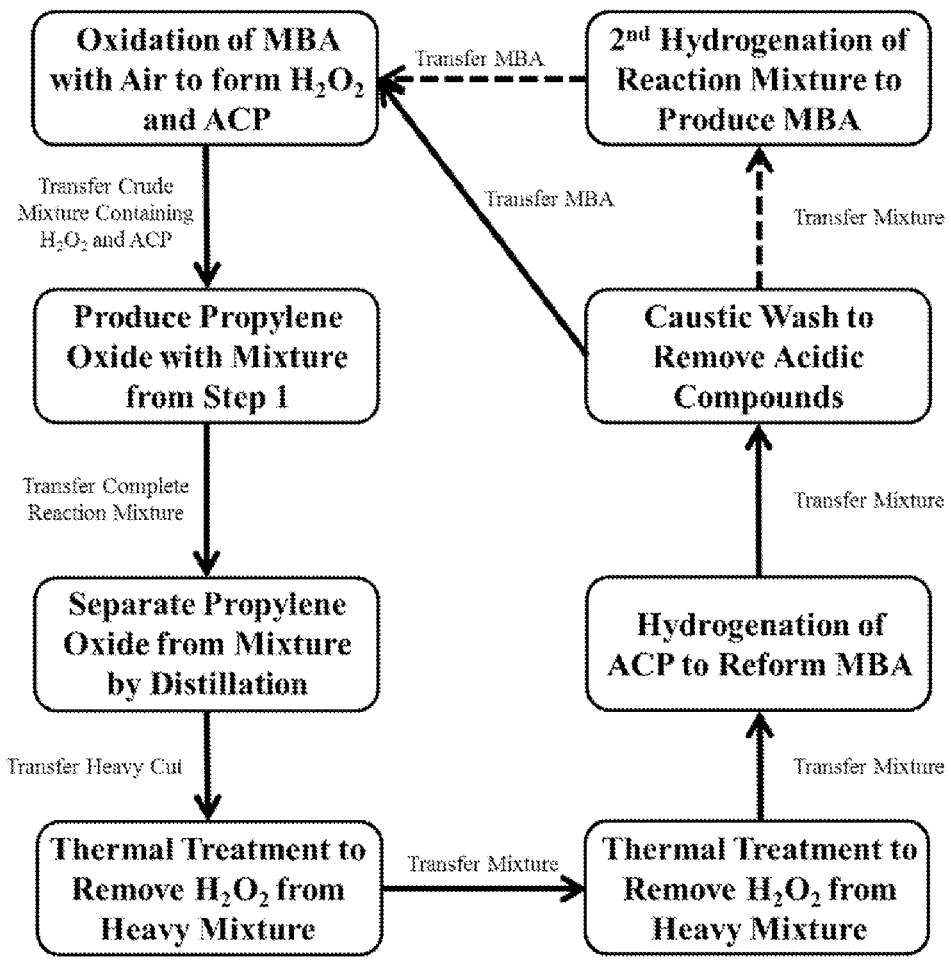
FIG. 1 provides a general overview of the epoxidation process. Optional steps are connected to the diagram through dotted arrows.

An embodiment corresponding to a non-limiting example of the complete reaction process is outlined in FIG. 1. In some aspects, the present disclosure presents a method of preparing an epoxide which eliminates co-products such as styrene and methyl tert-butyl ether (MTBE), and minimizes byproducts such as bis-alpha-methylbenzyl ether (BAMBE) and ring opening product such as glycols. In some embodiments, the reaction process may also be performed without the use of additional solvents such as methanol, which results in fewer reaction byproducts.

I. General Epoxidation Process

Figure 2:
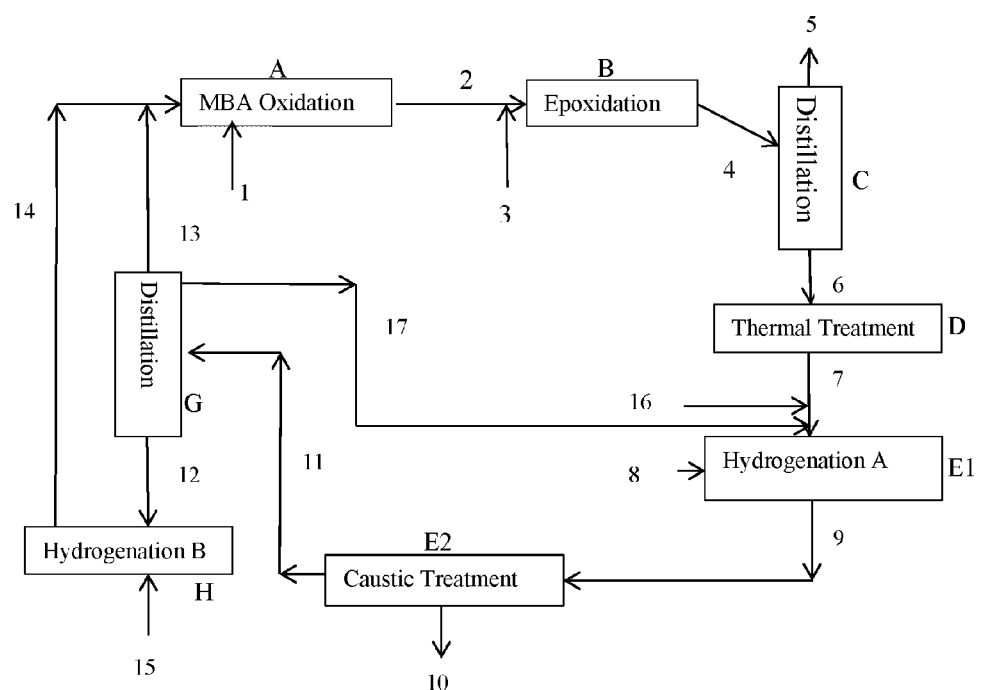
FIG. 2 shows a flow diagram of an example process setup for a reactor set up.

In some aspects, the present disclosure provides a method of preparing an epoxide from an alkene. In some embodiments, the alkene is propylene and the epoxide produced is propylene oxide. The process is described as shown in FIG. 1. In some embodiments, the process can be applied to a reactor scheme in a plant. In other embodiments, the process can be applied in a single reaction vessel. FIG. 2 shows one example of a possible reactor scheme in a flow diagram which can be applied for use with the epoxidation method. In the reactor A, the air is introduced via feed line 1 to oxidize the alpha-methylbenzyl alcohol to form hydrogen peroxide and acetophenone. The reaction mixture from A is transferred via 2 into the epoxidation reactor B, which contains catalyst and alkene introduced through feed line 3. The product from epoxidation reactor B is transferred via 4 to a distillation tower C, wherein the epoxide is removed from the reaction via outlet 5. The remaining materials are transported through 6 to a thermal treatment reactor D, wherein the unreacted hydrogen peroxide is broken down thermally. The reaction mixture is transported via 7. Alpha-methylbenzyl alcohol and acetophenone makeup is added via 16 to a hydrogenation reactor E1. Hydrogen gas is added to the reactor via feed line 8. After the hydrogenation of reaction mixture, the reaction mixture is transported via 9 to a caustic treatment E2. The caustic agent is added and the aqueous washes are removed from the reactor via 10. The reaction mixture is transported through the line 11 and into a distillation tower G and ethylbenzene is separated out and fed through line 17 into the reaction mixture being transported through feed line 7. Alpha-methylbenzyl alcohol is separated from the reaction mixture and returned to the air oxidation reactor A through feed line 13. The remaining heavy materials from distillation G are transported through feed line 12 and added to a second hydrogenation reactor H. Hydrogen gas is added to the reactor via line 15. The resultant mixture containing additional alpha-methylbenzyl alcohol is transported from the reactor H via 14 back into the air oxidation reactor A.

II. Overview of the Steps of the Epoxidation Process

A. Oxidation of an Alcohol to Form Hydrogen Peroxide

In some aspects of the present disclosure, the first step of the epoxidation process comprises reacting an alcohol with air to produce peroxide. In some aspects, the first step comprises the oxidation of alpha-methylbenzyl alcohol in the presence of air to form acetophenone and hydrogen peroxide. This irreversible reaction is shown in Scheme 4.

Scheme 4: Oxidation of Alpha-methylbenxyl Alcohol

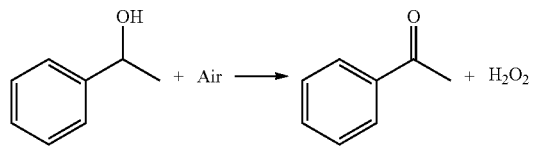

The alpha-methylbenzyl alcohol can be provided in a teed supply into the reactor such that the alpha-methylbenzyl alcohol contains less than 1% water, less than 10 ppm phenol and approximately 1% ethylbenzene. To the alpha-methylbenzyl alcohol, air or another source of oxygen is provided to the reactor in some aspects. Because of the reactivity of the produced hydrogen peroxide, an additive may be added to the reaction mixture. In some aspects, the additive is a sodium pyrophosphate, another metal pyrophosphate such as potassium pyrophosphate, lithium pyrophosphate, calcium pyrophosphate, magnesium pyrophosphate, beryllium pyrophosphate, sodium phosphate, potassium phosphate, lithium phosphate or tin stannate, or other basic chelating agents. Without being bound by theory, the addition of the additive may also improve the selectivity of the process by reducing $H_2O_2$ decomposition and by limiting the formation of undesirable byproducts such as bis-alpha-methyl-benzyl-ether (BAMBE). In some aspects, the oxidation of the alcohol is performed under certain specific conditions. The reaction comprises heating the reaction to a temperature from about 100° C. to about 160° C. In some embodiments, the temperature of the reaction is from about 120° C. to about 140° C. The reaction also comprises a reaction from about 2 to 150 psig (115 to 1,135 kPa). In some embodiments, the reaction pressure is from about 20 to 100 psig (240 to 790 kPa). Additionally, the reaction may comprises a liquid hour space velocity (LHSV) from about 0.16 to about 0.5 $hr^{-1}$ or has a liquid residence time of from about 2 to about 6 hours. In some embodiments, the LHSV is about 0.25 $hr^{-1}$ or the liquid residence time is about 4 hours. Finally, the air in the oxidation can be added multiple times to the reaction. In some embodiments, the air is added to the reaction 1, 2, 3, 4, 5, 6, 7, or 8 times or at this many different points. In some embodiments, the air is added to the reaction 2, 3, or 4 times or at this many different points. In some embodiments, the air is added to the reaction 3 times or at 3 different points.

In some aspects, the oxidation reaction results in the production of acetophenone and hydrogen peroxide. In some embodiments, the reaction converts the alpha-methylbenzyl alcohol to acetophenone at a conversion rate of about 10% to about 50%. The conversion of alpha-methylbenzyl alcohol is measured by the disappearance of alpha-methylbenzyl alcohol from the final reaction mixture. Similarly, conversion of the oxygen is measured by the disappearance of oxygen from the reaction mixture. The selectivity of the oxygen conversion is measured compared to the impurities produced compared to the amount of oxygen consumed. Similarity, the MBA selectivity is measured to the impurities produced compared to the amount of the alpha-methylbenzyl alcohol consumed. In some embodiments, greater than 80% of the alpha-methylbenzyl alcohol is converted to acetophenone and hydrogen peroxide. In some embodiments, greater than 95% of the alpha-methylbenzyl alcohol is converted to acetophenone and hydrogen peroxide. The conversion of oxygen in the air in the air occurs at greater than 80%. In some embodiments, the conversion of oxygen is greater than 90%. In some embodiments, the byproducts of the reaction include phenol and bis-alpha-methyl benzyl ether (BAMBE). In some embodiments, the reaction produces less than 2% of either of these byproducts. In some embodiments, the reaction produces about 1% BAMBE. In some embodiments, the reaction produces less than about 1% phenol. In some embodiments, greater than 80% of the oxygen is converted into hydrogen peroxide. In some embodiments, from about 40% to about 80% of the remaining oxygen is converted into water. In some embodiments, about 14% of the total oxygen is converted into water.

It is also envisioned that the oxidizing agent in the epoxidation step is a hydrogen peroxide which may be generated through the oxidation of an alcohol such as isopropanol. The hydrogen peroxide may be generated before the addition to the epoxidation reaction or the hydrogen peroxide may be generated in situ. In some embodiments, the hydrogen peroxide can also be generated through the anthraquinone process or through the direct conversion of hydrogen and oxygen to form hydrogen peroxide. In some embodiments, the concentration of the hydrogen peroxide is from about 0.1% to about 90% by weight hydrogen peroxide in water. In certain embodiments, the concentration of hydrogen peroxide is from about 1 to 10 weight percent hydrogen peroxide. In further embodiments, the hydrogen peroxide is generated via the reaction of an oxygen and a hydrogen source with a transition metal catalyst. In some embodiments, the hydrogen and oxygen source is molecular hydrogen and molecular oxygen, respectively.

B. Epoxidation of an Alkene

In some aspects of the present disclosure, the second step of the reaction comprises transferring the crude reaction from A with an alkene and a catalyst to form an epoxide. In some embodiments, the alkene is an alkene with between 2 and 30 carbon atoms. The alkene may also be substituted as described herein. Alkenes with more than one double bond can also be used in the method described. In some embodiments, the present method relates to the conversion of propylene into propylene oxide. In some non-limiting embodiments, the alkene of the present disclosure includes but is not limited to ethylene, propylene, butene, pentene, hexene, heptene, octene, nonene or decene. In some embodiments, the corresponding epoxide is produced for each of these reactions such as ethylene oxide, propylene oxide, butene oxide, pentene oxide, hexene oxide, heptene oxide, octene oxide, nonene oxide or decene oxide. In some aspects, the reaction mixture can comprise the unoxidized alcohol, the oxidized alcohol and an oxidizing agent. In some embodiments, the alcohol present in the first step could be alpha-methylbenzyl alcohol (1-phenylethyl alcohol), cyclohexanol, isopropyl alcohol and/or tert-butyl alcohol. Additionally, the reaction mixture can also contain ketones such as acetone, acetophenone or cyclohexanone. The epoxidation reaction can be carried out in the liquid phase, liquid $CO_2$ in the subcritical or supercritical form, oxygenated hydrocarbons including alcohols, esters, ethers, and ketones, nitriles, aromatic or aliphatic hydrocarbon, water and/or combinations thereof. Specific solvents utilized in the process may include nitriles, alcohols and ketones. In some embodiments, the epoxidation reaction comprises a mixture of solvents including mixtures of water and an organic solvent(s). Additionally, alpha-methylbenzyl alcohol (1-phenylethyl alcohol), cyclohexanol, isopropyl alcohol, tert-butyl alcohol, acetonitrile, glyme, dimethyl ethylene glycol ether, dioxane, trioxane, acetophenone, acetone and/or cyclohexanone are used as solvents in some embodiments of the present disclosure. Additional solvents are described in U.S. Pat. No. 8,124,555, the contents of which are incorporated herein by reference in its entirety. Additionally, the oxidizing agent used in the epoxidation step includes but is not limited to hydrogen peroxide, alkyl, cycloalkyl, aryl and aralkyl hydroperoxides such as methyl benzyl hydroperoxide, tert-butyl hydroperoxide, cyclohexyl hydroperoxide and cumyl hydroperoxide.

Figure 3:
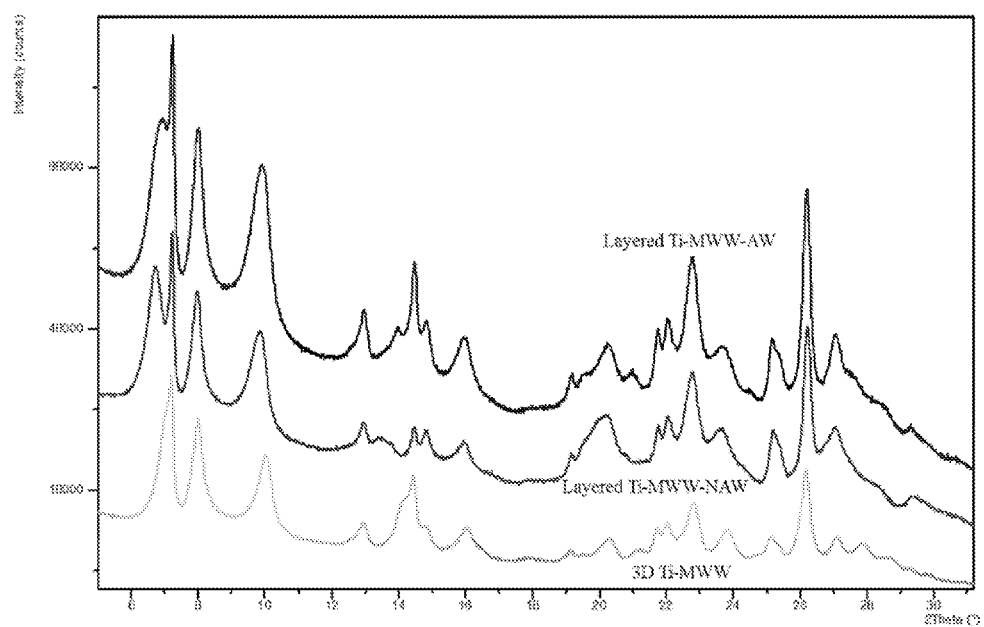
FIG. 3 shows XRD spectra of titanium MWW catalysts including TiMWW catalyst (3D Ti-MWW), Non-acid washed layered TiMWW catalyst (Layered TiMWW-NAW), and layered TiMWW catalyst which has been washed with an acid (Layered TiMWW-AW).

In some aspects of the present disclosure, the epoxidation reaction further comprises a catalyst. In some embodiments, the catalyst is a titanium catalyst wherein the titanium is impregnated on a solid support. The titanium catalyst may be TiMWW or a layered TiMWW wherein the titanium is impregnated in an aluminosilicate MWW zeolite. In some embodiments, the TiMWW catalyst has an XRD spectra as is shown in FIG. 3. The method of preparation of a TiMWW catalyst is known to one of skill in the art. In some aspects, the preparation has been taught in, for example, in U.S. Pat. No. 6,759,540; Wu, et al., 2001; and U.S. Pat. Nos. 8,124, 555 and 8,440,846. The titanium MWW zeolite catalyst principally comprises titanium, silicon and oxygen but the catalyst may also comprise boron and/or small amounts of iron, aluminum, sodium, potassium, copper, or other similar elements. Post treatment of TiMWW with a template yields layered TiMWW-NAW. Washing TiMWW-NAW with an acid yields layered TiMWW-AW. The layered TiMWW-NAW can also be prepared via hydrothermal synthesis of silica, tetrabutyl orthotitanate and a template in the presence of crystallization agent such as boric acid. The layered Ti-MWW-AW can then be obtained by refluxing layered Ti-MWW-NAW with a $HNO_3$ or $H_2SO_4$ solution. Since boron is detrimental to the catalyst activity, the post treatment method for the synthesis of layered Ti-MWW is often preferred because the catalyst contains minimal amounts of boron in the sample.

Such titanium MWW zeolite catalysts may have the empirical formula $xTiO_2.(1-x)SiO_2$, wherein x is a numeral from about 0.0001 and about 0.5. In some embodiments, x is from about 0.01 to about 0.125. In another embodiment, the ratio of Si:Ti may range from about 9.5:1 to about 99:1. In some embodiments, the ratio may be from about 9.5:1 to about 60:1. In particular embodiments, it is envisioned that titanium rich MWW catalysts may be desirable.

The epoxidation process described in the present disclosure may use a catalyst which is either a powder or a large particle size solid. In some embodiments, the zeolite catalyst may be in the form of a powder but it is also contemplated that the zeolite catalyst can be used if spray dried, pelletized or extruded. Additionally, the zeolite catalyst may also further comprise a binder before the catalyst is shaped, spray dried, molded or extruded into a particular desired form. Additionally, the catalyst in some embodiments is either in a suspension or a fixed-bed form.

In another embodiment, a layered TiMWW catalyst is used to epoxidize the alkene. The layered TiMWW catalyst may be used with a template to prepare the catalyst. Some templating agents that may be used in some embodiments are piperidine, hexamethyleneimine and/or adamantyl ammonium hydroxide, octyltrimethylammonium hydroxide, hetyltrimethylammonium hydroxide, hexyltrimethylammonium hydroxide, hexyltrimethylammonium hydroxide or trimethyladamantylammonium hydroxide. In some embodiments, the templating agent is hexamethyleneimine or piperidine. In one embodiment, the templating agent is piperidine. After reaction of the TiMWW catalyst with the templating agent, in some embodiments, the catalyst is washed with an acid. In some aspects, the acids that the catalyst can be washed with include nitric acid, hydrochloric acid, sulfuric acid, sulfurous acid, phosphoric acid and ammonium chloride. In some embodiments, the TiMWW catalyst and the layered TiMWW catalyst have the XRD spectra as shown FIG. 3.

Additionally, in some embodiments, the reaction mixture may additionally comprise a buffer. Without being bound by theory, the addition of buffer is believed to be beneficial in increasing the catalytic activity, reducing the ring opening byproducts, or increasing catalytic specificity. In some embodiments, the pH of the buffer solution is from about 3 to about 12. In further embodiments, the pH of the solution is from about 4 to about 10 and additional embodiments, the pH is from about 5 to about 9. The buffer is comprised of a cation and an anion. In some aspects, the cation includes ammonium, alkylammonium such as a tetraalkylammonium or a pyridinium salt, alkali metal and alkaline earth metals. Some non-limiting examples of cations that can be used in the buffer include $NH_4^+$, $NMe_4^+$, $NBu_4^+$, $Li^+$, $Na^+$, $K^+$, $Mg^{++}$, $Cs^+$ or $Ca^{++}$. Additionally, the anion, in some embodiments, include phosphate, carbonate, bicarbonate, carboxylates such as acetate, phthalate, oxalate, or citrate, borate, hydroxide, silicate or aluminosilicate. Some potential additives of the buffer include ammonium acetate, ammonium benzoate, sodium acetate, sodium benzoate, ammonium dihydrogen phosphate, sodium dihydrogen phosphate, potassium acetate, potassium benzoate or potassium dihydrogen phosphate. In some embodiments, the epoxidation step includes the addition of ammonia or ammonium hydroxide to balance the pH of the reaction. In some embodiments, the buffer is added to the reaction in a concentration from about 0.0001 M to about 1 M. In a more embodiments, the buffer is added to the reaction in a concentration from about 0.0005 M to about 0.3 M.

In some embodiments, the reaction of the oxidizing agent with the alkene is run with a molar ratio of alkene to oxidizing agent from about 1:100 to about 100:1. In further embodiments, the molar ratio is from about 1:20 to about 20:1, about 1:5 to about 18:1, about 1:1 to about 15:1 and about 3:1 to about 10:1. Without being bound by theory, it is believed that at least one equivalent of an oxidizing agent is need to oxidize the alkene. While at least one equivalent of the oxidizing agent is needed to react with the alkene, in some embodiments, more than one equivalent of one of the materials is used to enhance the yield of the reaction. Additionally, in some embodiments the reaction is run under a pressure from about 20 to about 1200 pounds per square inch. In further embodiments, the pressure of the reaction is from about 50 to about 1000 pounds per square inch, about 80 pounds per square inch to about 800 pounds per square inch and about 100 pounds per square inch to 500 pounds per square inch. Additionally, the temperature of the reaction may be modulated to improve yield or selectivity. In some embodiments, the temperature is from about ambient temperature to about 250° C. In certain embodiments, the temperature is from about 20° C. to about 150° C., about 20° C. to about 100° C. and about 50° C. to about 80° C. In some embodiments of the present disclosure, the alcohol and ketone are present in a weight ratio from no alcohol and about 100% ketone to about 100% alcohol and no ketone. Conversely, the weight ratio of hydrogen peroxide to water in some embodiments is from 0.1:99.9 to 90:10. In some embodiments, the weight ratio is from 1:99 to 10:90. In some embodiments, the weight ratio of alpha-methylbenzyl alcohol to acetophenone to hydrogen peroxide to water from the oxidation in A is from 96:1:2.9:0.1 to 44:44:11.7:0.3 and from about 76:18.9:5:0.1 to about 54:36:9.7:0.3. In some embodiments, the weight ratio described by the present disclosure is about 64:29:6.3:0.7.

In some embodiments of the present method, a carrier gas is used. An appropriate carrier gas should be inert to the reaction conditions. Some non-limiting examples of carrier gases include helium, neon, argon, other noble gases, nitrogen, carbon dioxide or alkanes with between 1 and 8 carbon atoms. In some embodiments, the carrier gases include nitrogen or an alkane with between 1 and 4 carbon atoms. In some embodiments, the carrier gas comprises a mixture of two, three or more individual carrier gases. Furthermore, when the alkene is propylene and the carrier gas is propane, in some embodiments, the addition of the carrier gas must be controlled and added at specific time points.

In some embodiments of the present disclosure, the method is used in a batch, continuous or a semi-continuous process with the appropriate selection of reactor vessel. An appropriate reaction vessel includes but is not limited to a fixed bed, transport bed, fluidized bed, stirred slurry or CSTR reactor.

In some embodiments, the order of addition of the reaction materials may achieve high efficacy and selectivity of products. In some embodiments of the method, the catalyst is first added to the crude mixture from section A of the present disclosure. In some embodiments, the method then comprises adding the alkene to the mixture. Finally, in some embodiments, a buffer is optionally added to the reaction mixture. In some embodiments, the crude mixture of A is also purified before the mixture is added to the reaction.

TiMWW has been shown to be an effective epoxidation catalyst in solvents other than methanol. The catalyst has good activity and selectivity for the epoxidation of propylene with hydrogen peroxide in large molecule solvents such as tert-butanol (TBA), alpha-methylbenzyl alcohol or acetophenone. When large molecule solvents are used as the solvent for the reaction, smaller and minimal amounts of ring opening products are formed. Furthermore, the addition of a small amount of buffer further improves catalyst activity and selectivity. In addition, the layered TiMWW, which is prepared via post treatment of TiMWW with piperidine or with piperidine and acid wash, is also shown to be more effective than TiMWW in propylene epoxidation in these solvents.

C. Separation of the Epoxide

In some aspects of the present disclosure, the third step of the reaction comprises separating the epoxide from the other components of the reaction mixture. In some embodiments, the epoxide is separated from the reaction mixture based upon a physical property such as boiling point or solubility. The propylene oxide produced in section B may be separated from the crude reaction mixture through the use of distillation. In some embodiments, the distillation is performed at a temperature from about 40° C. to about 170° C.

D. Thermal Decomposition of the Peroxide

In some aspects of the present disclosure, the fourth step of the reaction comprises decomposing the peroxide formed using heat. In some embodiments, the method of peroxide decomposition is using heat. The decomposition of the peroxide comprises heating the reaction mixture to a temperature from about 100° C. to about 250° C., in some embodiments. The temperature in some embodiments is from about 150° C. to about 200° C., such as about 170° C. Additionally, the thermal decomposition reaction proceeds for a time period from about 15 minutes to about 2 hours, from about 30 minutes to one hour, such as about 45 minutes. Finally, the thermal decomposition of the peroxide may occur at a pressure from about 50 pounds per square inch to about 300 pounds per square inch, from about 100 pounds per square inch to about 200 pounds per square inch and from about 125 to about 150 pounds per square inch, such as about 130 pounds per square inch.

E. Hydrogenation of Acetophenone to Form Alpha-Methylbenzyl Alcohol

In some aspects of the present disclosure, the fifth step of the reaction comprises hydrogenating the reaction mixture to reduce the acetophenone to form alpha-methylbenzyl alcohol. In some embodiments, the hydrogenation reaction comprises adding a hydrogenation catalyst. Potential hydrogenation reaction catalysts may include transition metal catalysts with a palladium (Pd) or copper (Cu) centers. Some specific transition metal catalysts include KL7752, copper chromite, nickel, platinum, ruthenium, rhodium and POSM acetophenone hydrogenation catalyst. Without being bound by theory, the addition of ethylbenzene to the hydrogenation of the acetophenone may improve the efficacy of the hydrogenation activity of the catalyst and the solubility of hydrogen gas. Furthermore, the hydrogenation of the acetophenone also reduces the byproducts of the reaction. In some embodiments, the hydrogenation method comprises heating the reaction mixture to a temperature from about 50° C. to about 120° C. and from about 70° C. to about 100° C., such as about 85° C. In some embodiments, the hydrogenation method comprises a pressure from about 200 pounds per square inch to about 500 pounds per square inch and about 250 pounds per square inch to about 350 pounds per square inch, such as about 335 pounds per square inch.

In some aspects of the present disclosure, the hydrogenation reaction comprises a weighted hourly space velocity from about 10 to about 15 hr$^{-1}$, such as about 12 hr$^{-1}$. The weighted hourly space velocity is calculated by dividing the mass flow of the acetophenone plus alpha-methylbenzyl alcohol divided by the mass of the catalyst. The acetophenone conversion during the reaction may be greater than 75%, such as equal to or greater than 90%, based upon the amount of acetophenone removed from the reaction mixture. The hydrogenation reaction of acetophenone further comprises adding ethylbenzene to the reaction mixture in some embodiments. In some embodiments, the reaction comprises adding between 1% to about 50% ethylbenzene to the reaction mixture, such as adding 30% ethylbenzene to the reaction mixture.

F. Caustic Wash of Hydrogenated Material to Remove Acids

In some aspects of the present disclosure, the sixth step of the reaction comprises washing the hydrogenated material with a caustic wash to remove acidic materials from the reaction mixture. Some of the acidic materials removed from the reaction mixture during the caustic wash may include acetic acid, formic acid, phenol, ethyl phenol or other acidic or phenolic compounds. In some embodiments, the caustic wash is performed at a temperature from about ambient temperature to about 100° C. and from about 40° C. to about 80° C., such as about 60° C. Furthermore, the wash is performed under pressure in some aspects. In some embodiments, the pressure of the reaction is from about 75 pounds per square inch to about 250 pounds per square inch and from about 125 pounds per square inch to about 175 pounds per square inch, such as about 150 pounds per square inch. Additionally, without being bound by theory, the weight ratio of organic material (organic layer) to caustic agents (aqueous layer) for effectively removing the acidic and phenolic compound may be from about 1:4 to about 8:1 and about 1:1 to about 6:1, including about 4:1.

Additionally, the concentration of the caustic material needed to effectively remove the acidic materials from the reaction mixture may vary. In some embodiments, the strength of the caustic materials is from about 0.1% to about 5% and from about 0.25% to about 1%. In certain embodiments, the ethylbenzene concentration in the organic material (organic layer) is about 45% by weight. Without being bound by theory, the concentration of about 45% ethylbenzene is needed to ensure a clean separation between the two phases (e.g., the organic layer/phase and the aqueous layer/phase). In some embodiments, the excess ethylbenzene is removed from the reaction mixture before the alcohol is returned to A. In some embodiments, the ethylbenzene is removed from the reaction by distillation. The final reaction material may comprise a concentration of phenol of less than 100 ppm. In some embodiments, the concentration of phenol is less than 50 ppm, such as less than about 10 ppm. When this step is performed in a reactor step-up, the caustic contactor is performed in a countercurrent flow which contains at least 4 equilibrium stages. In some embodiments, the reactor contains at least 4, 5, 6, 7 or 8 equilibrium stages.

G. Recovery of Alpha-Methylbenzyl Alcohol from Reaction Mixture

In some aspects of the present disclosure, the seventh step of the reaction comprises recovering the alpha-methylbenzyl alcohol from other heavy materials. In some embodiments, the alpha-methylbenzyl alcohol is recovered from the reaction mixture via distillation. In some embodiments, the distillation is performed at a temperature from 50° C. to about 150° C.

H. Hydrogenation of Heavy Materials to Remove BAMBE

In some embodiments, the recovery of alpha-methyl benzyl alcohol (1-phenylethyl alcohol) further comprises reacting the other heavy materials remaining after distillation, such as bis-alpha-methylbenzyl ether (BAMBE), with a hydrogenation catalyst including but not limited to rhodium, ruthenium, palladium, Encat 30NP, LK7752, palladium based on carbon support, alumina or a polymer support. In some embodiment, the reaction comprises adding hydrogen gas. The reaction also may comprise a temperature from about ambient temperature to about 80° C. and a pressure from about 1 pound per square inch to about 500 pounds per square inch. In some embodiments, the temperature is from about 40° C. to about 80° C., such as from about 50° C. to about 60° C. In some embodiments, the pressure is about 50 pounds per square inch to about 300 pounds per square inch, including about 100 pounds per square inch to about 250 pounds per square inch. The conversion of the acetophenone to alpha-methylbenzyl alcohol (1-phenylethyl alcohol) and the recovery of alpha-methylbenzyl alcohol may be from about 1% to about 100%, such as greater than 50%. In some embodiments, the conversion is greater than 80%. In some embodiments, hydrogenation may include an additional reaction to remove BAMBE (bis-alpha-methylbenzyl ether). In some embodiments, the reaction above hydrogenates the BAMBE to remove and reform alpha-methylbenzyl alcohol and ethylbenzene.

I. Recycling Alpha-Methylbenzyl Alcohol into A

In some aspects of the present disclosure, the reaction comprises returning the alpha-methylbenzyl alcohol recovered into the initial oxidation.

III. Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

IV. Definitions

When used in the context of a chemical group, "hydrogen" means —H; "hydroxy" means —OH; "oxo" means =O; "carbonyl" means —C(=O)—; "carboxy"

means C(=O)OH (also written as —COOH or —CO₂H); "halo" means independently —F, —Cl, —Br or —I; and "amino" means —NH₂. When used in the context of a chemical group, "carboxylate" means a molecule which contains the group, —C(=O)O⁻ (also written as C(O)O⁻ or —CO₂⁻) and the overall charge of the molecule is negative, and "halide" means a halogen atom formulated as an anion bearing a single negative charge. Any undefined valency on an atom of a structure shown in this application implicitly represents a hydrogen atom bonded to that atom.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the formula

includes

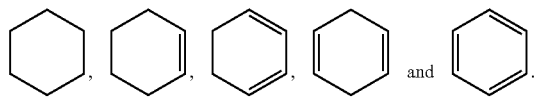

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂" means a single bond where the group attached to the thick end of the wedge is "out of the page." The symbol "⦀" means a single bond where the group attached to the thick end of the wedge is "into the page". The symbol "∿" means a single bond where the geometry around a double bond (e.g., either E or Z) is undefined. Both options, as well as combinations thereof are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M----C, and M====C, each refer to a bond of any type and order between a metal atom and a carbon atom.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene $_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bonds or a carbon nitrogen double bond may be present. When such a bond is present, then carbon-carbon double bonds that may occur as part of keto-enol tautomerism or imine/enamine tautomerism are not precluded.

The term "aliphatic" when used without the "substituted" modifier signifies that the compound/group is acyclic or cyclic, but non-aromatic hydrocarbon compound or group. In aliphatic compounds/groups, the carbon atoms can be joined together in straight chains, branched chains or non-aromatic rings (alicyclic). Aliphatic compounds/groups can be saturated, i.e. joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures, wherein the cycloalkyl group consists of no atoms other than carbon and hydrogen. As used herein, the term does not preclude the presence of one or more alkyl groups (carbon number limitation permitting) attached to the ring or ring system. The groups —CH₃ (Me), —CH₂CH₃ (Et), —CH₂CH₂CH₃ (n-Pr or propyl), —CH(CH₃)₂ (i-Pr, ⁱPr or isopropyl), —CH(CH₂)₂ (cyclopropyl), —CH₂CH₂CH₂CH₃ (n-Bu), —CH(CH₃)CH₂CH₃ (sec-butyl), —CH₂CH(CH₃)₂ (isobutyl), —C(CH₃)₃ (tert-butyl, t-butyl, t-Bu or ᵗBu), —CH₂C(CH₃)₃ (neo-pentyl), cyclobutyl, cyclopentyl, cyclohexyl and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH₂— (methylene), —CH₂CH₂—, —CH₂C(CH₃)₂CH₂—, —CH₂CH₂CH₂—, and

are non-limiting examples of alkanediyl groups. It is noted that while the alkenediyl group is aliphatic, once connected at both ends, this group is not precluded from forming an aromatic structure. The term "alkylidene" when used without the "substituted" modifier refers to the divalent group =CRR', in which R and R' are independently hydrogen, alkyl or R and R' are taken together to represent an alkanediyl having at least two carbon atoms. Non-limiting examples of alkylidene groups include =CH₂, =CH(CH₂CH₃) and =C(CH₃)₂. An "alkane" refers to the general compound H—R, wherein R is alkyl as defined above. When any of these terms is used with the "substituted" modifier one or more hydrogen atoms has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃ or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" refers to a subset of substituted alkyls, in which one or more hydrogen atoms has been substituted with a halo group and no other atoms aside from carbon, hydrogen and halogen are present. The group —CH₂Cl is a non-limiting example of a haloalkyl. The term "fluoroalkyl" refers to a subset of substituted alkyls, in which one or more hydrogen has been substituted with a fluoro group and no other atoms aside from carbon, hydrogen and fluorine are present. The groups —CH₂F, —CF₃, and —CH₂CF₃ are non-limiting examples of fluoroalkyl groups.

The term "alkenyl" when used without the "substituted" modifier refers to a monovalent unsaturated aliphatic group with a carbon atom as the point of attachment, a linear or branched, cyclo, cyclic or acyclic structure, at least one nonaromatic carbon-carbon double bond, no carbon-carbon triple bonds and no atoms other than carbon and hydrogen. Non-limiting examples of alkenyl groups include —CH=CH₂ (vinyl), —CH=CHCH₃, —CH=CHCH₂CH₃, —CH₂CH=CH₂ (allyl), —CH₂CH=CHCH₃ and —CH=CHCH=CH₂. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds and no atoms other than carbon and hydrogen. The groups —CH=CH—, —CH=C(CH₃)CH₂—, —CH=CHCH₂—, and

are non-limiting examples of alkenediyl groups. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —CH=CHF, —CH=CHCl and —CH=CHBr are non-limiting examples of substituted alkenyl groups.

The term "aryl" when used without the "substituted" modifier refers to a monovalent unsaturated aromatic group with an aromatic carbon atom as the point of attachment, with the carbon atom forming part of one or more six-membered aromatic ring structures, wherein the ring atoms are all carbon and the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl or alkenediyl groups (carbon number limitation permitting). Non-limiting examples of arenediyl groups include:

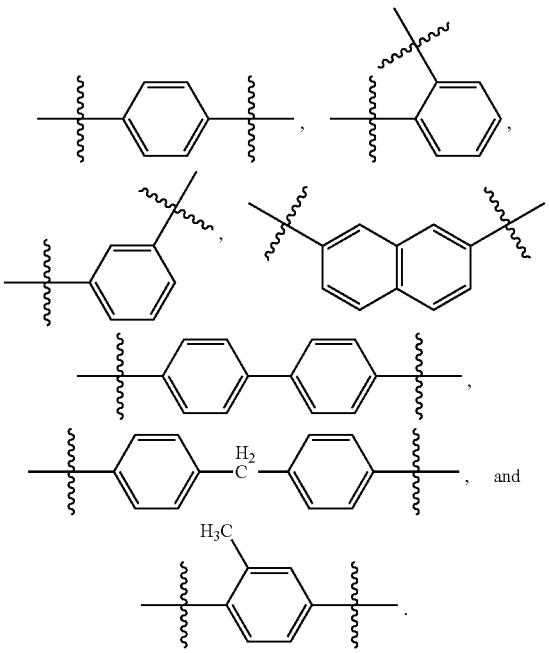

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃ or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$ or —S(O)$_2$NH$_2$. Non-limiting examples of substituted aralkyls are (3-chlorophenyl)-methyl and 2-chloro-2-phenyl-eth-1-yl.

The term "aralkenyl" when used without the "substituted" modifier refers to the monovalent group -alkenediyl-aryl, in which the terms alkenediyl and aryl are each used in a manner consistent with the definitions provided above. Non-limiting examples of aralkenyls are 2-phenylethenyl and 3,3-diphenyl-prop-2-enyl. The term "aralkene" refer to a compound having the formula H—R, wherein R is aralkenyl as this term is defined above. A "terminal aralkene" refers to an aralkene having just one non-aromatic carbon-carbon double bond, wherein that bond forms a vinyl group at one end of the molecule. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$ or —S(O)$_2$NH$_2$. Non-limiting examples of substituted aralkenyls are (3-nitrophenyl)-ethenyl and 4-cyano-4-phenyl-but-1-enyl.

The use of the word "a" or "an," when used in conjunction with the term "comprising" in the claims and/or the specification may mean "one," but it is also consistent with the meaning of "one or more," "at least one" and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "epoxide" refers to a three-membered ring containing at least one oxygen atom and two carbon atoms joined by single bonds. An "epoxidation reaction" is a reaction which leads to generation of an epoxide on the molecule. The most common epoxidation reaction results from converting an alkene or aralkene functional group within a molecule into an epoxide group.

An "isomer" of a first compound is a separate compound in which each molecule contains the same constituent atoms as the first compound, but where the configuration of those atoms in three dimensions differs.

A "method" is series of one or more steps undertaking lead to a final product, result or outcome. As used herein, the word "method" is used interchangeably with the word "process".

A "peroxide" is a molecule containing a single covalent bond between two oxygen atoms and each oxygen is also bound to a hydrogen, alkyl, aryl or aralkyl group as those groups are defined above and contains between 1 and 30 carbon atoms. In some embodiments, a hydroperoxide is a compound containing a single covalent bond between two oxygen atoms, one of the oxygen atoms is bound to a hydrogen atom and the other oxygen is bound to an alkyl, aryl or aralkyl group as those groups are defined above, and contains between 1 and 20 carbon atoms. Some non-limiting examples of hydroperoxides include ethylbenzene hydroperoxide, tert-amylhydroperoxide, cyclohexyl hydroperoxide and cumene hydroperoxide. In general, the peroxide bond between the two oxygen atoms is labile and readily decomposes or reacts with other molecules. Some non-limiting examples of peroxides include HO—OH (hydrogen peroxide), (CH$_3$)$_3$CO—OH (tert-butyl hydroperoxide) and C$_6$H$_5$CHO$_2$HCH$_3$.

The "peroxide conversion percentage" is a measurement of the amount of peroxide consumed in the reaction. This measurement can be used to compare the efficacy of a given reaction and as a measure of the amount of reagent consumed in the production of the desired product.

A "solid support" or "carrier" relate to an inert material which does not react with the substrate or reagents. In some instances, the solid support or carrier can be silica, alumina, organic polymers or other non-reactive materials with a high surface area and a high porosity. Additionally, in some embodiments, the solid support or carrier contains numerous pores, voids or other interstices throughout their structures. In some embodiments, the silica particles may contain particles which are flocculated or linked together into a dense, close-packed mass or contain a loosely knit structure and readily disintegrated into open-packed aggregates. The support or carrier can be used to bind the catalytically active atoms or complexes. In some embodiments, the major portion of the solid support is silicon dioxide (SiO$_2$) and amorphous forms of SiO$_2$. In some non-limiting examples, the solid support is a silica compound that is commercially available for various purposes including, but not limited to, thin layer chromatography (TLC), column chromatography, catalyst support or other commercial uses. In some instances, the solid support is a silica gel or zeolite such as the Davisil® 643 porous material. In some embodiments, the solid support is a mesoporous silica such as molecular sieves.

The above definitions supersede any conflicting definition in any reference that is incorporated by reference herein. The fact that certain terms are defined, however, should not be considered as indicative that any term that is undefined is indefinite.

EXAMPLES

The following examples are included to demonstrate certain embodiments. It should be appreciated by those of skill in the art that the techniques disclosed in the examples which follow represent techniques intended to function well in the practice of the embodiments as provided herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the appended claims.

Example 1

Conversion of Alcohol into Peroxide and Propylene Oxide Conversion

TABLE 1

Peroxide Conversion and Selectivity of $H_2O_2$ Utilization

| Sample | Zeolite Catalyst | Solvent | Buffer | Temp (° C.) | $H_2O_2$ conversion (%) | Ring Opening (%) | $H_2O_2$ selectivity to PO (%) |
|---|---|---|---|---|---|---|---|
| 1 | TS-1 | methanol/water | — | 50 | 48 | — | 78 |
| 2 | TS-1 | methanol/water | Ammonium acetate | 50 | 15 | — | 68 |
| 3 | TS-1 | t-butyl alcohol/water | — | 50 | 12 | — | 58 |
| 4 | TS-1 | t-butyl alcohol/water | Ammonium dihydrogen phosphate | 50 | 11 | — | 15 |
| 5 | TS-1 | Acetonitrile/water | — | 50 | 7 | — | 92 |
| 6 | TS-1 | Acetonitrile/water | Ammonium dihydrogen phosphate | 50 | 4 | — | 100 |
| 7 | TiMWW | t-butyl alcohol/water | — | 50 | 43 | 0.6 | 75 |
| 8 | TiMWW | t-butyl alcohol/water | Ammonium dihydrogen phosphate | 50 | 99 | 0.3 | 80 |
| 9 | TiMWW | 1-phenylethyl alcohol/acetophenone | — | 70 | 20.9 | 1.72 | 93 |
| 10 | TiMWW | 1-phenylethyl alcohol/acetophenone | Ammonium acetate | 70 | 99.2 | 0.33 | 99 |
| 11 | TiMWW | 1-phenylethyl alcohol/acetophenone | Ammonium dihydorgen phosphate | 70 | 96.8 | 0.331 | 97 |

As shown in Table 1, the epoxidation catalyst, TS-1, with small molecule solvents such as methanol leads to moderate hydrogen peroxide conversion as can be seen in Sample 1 but $H_2O_2$ conversion was reduced when TS-1 is used with a buffer (Compare Sample 2 vs. Sample 1). Additionally, other solvents like large molecule solvents, like acetonitrile and t-BuOH, also lead to a reduction of hydrogen peroxide conversion compared to methanol (Samples 3 and 5 vs. Sample 1). Finally, when both the large molecule solvents are used in conjunction with a buffer, the amount of hydrogen peroxide conversion level was further reduced (Samples 4 and 6 vs. Sample 1 and Samples 3 and 5).

On the other hand, the epoxidation catalyst, TiMWW, gave a similar hydrogen peroxide conversion to the TS-1 catalyst (Sample 7 vs. Sample 1). Additionally, the use of TiMWW with 1-phenylethyl alcohol and acetophenone leads to lowered hydrogen peroxide conversion (Sample 9 vs. Sample 1). On the other hand, the use of TiMWW in the presence of a buffer with t-butyl alcohol and water or with 1-phenylethyl alcohol and acetophenone lead to a greatly increased hydrogen peroxide conversion as well as hydrogen peroxide selectivity to propylene oxide and reduced ring opening by-products. (Samples 8, 10, and 11 vs. Samples 7 and 9).

TABLE 2

Mass Balance of Particular Component Streams in FIG. 2 (lb/hr)

| Stream or Component | 1 lb/hr (kg/hr) | 2 lb/hr (kg/hr) | 3 lb/hr (kg/hr) | 4 lb/hr (kg/hr) | 5 lb/hr (kg/hr) | 6 lb/hr (kg/hr) | 7 lb/hr (kg/hr) | 8 lb/hr (kg/hr) | 9 lb/hr (kg/hr) |
|---|---|---|---|---|---|---|---|---|---|
| $H_2$ | — | — | — | — | — | — | — | 4,278 (1,940) | — |
| $N_2$ | 249,910 (113,357) | — | — | — | — | — | — | — | — |
| $O_2$ | 66,432 (30,133) | — | — | — | — | — | — | — | — |
| Propylene | — | — | 70,590 (32,019) | 237 (107) | 237 (107) | — | — | — | — |
| Propylene oxide | — | — | — | 96,131 (43,604) | 96,131 (43,604) | — | — | — | — |
| MBA-PG ether | — | 782 (354.7) | — | 1,159 (525) | — | 1,159 (525) | 1,159 (525) | — | 1,159 (525) |
| $H_2O_2$ | — | 57,918 (26,271) | — | — | — | — | — | — | — |
| $H_2O$ | — | 5,906 (2,678.9) | — | 36,317 (16,473) | 32,686 (14,826) | 3,632 (1,647) | 4,946 (2,243) | — | 5,377 (2,439) |
| Formic Acid | — | 336 (152) | — | 336 (152) | — | 336 (152) | 336 (152) | — | 339 (154) |

TABLE 2-continued

Mass Balance of Particular Component Streams in FIG. 2 (lb/hr)

| | | | | | | | | |
|---|---|---|---|---|---|---|---|---|
| Acetic Acid | — | 375 (170) | — | 375 (170) | — | 375 (170) | 375 (170) | — | 379 (172) |
| Ethyl-benzene | — | 2,653 (1,203) | — | 2,653 (1,203) | — | 2,653 (1,203) | 2,888 (1,310) | — | 386,476 (175,302) |
| MBA | — | 593,856 (269,368) | — | 593,601 (269,252) | — | 593,601 (269,252) | 591,368 (268,240) | — | 864,872 (392,299) |
| Aceto-phenone | — | 271,270 (123,046) | — | 271,270 (123,046) | — | 271,270 (123,046) | 279,530 (126,793) | — | 28,009 (12,705) |
| Phenol | — | 1,277 (579) | — | 1,277 (579) | — | 1,277 (579) | 1,277 (579) | — | 1,292 (586) |
| EBHP | — | 5,180 (2,349.6) | — | 5,180 (2,349.6) | — | 5,180 (2,349.6) | 0 | — | — |
| BAMBE | — | 9,069 (4,113.6) | — | 9,069 (4,113.6) | — | 9,069 (4,113.6) | 9,069 (4,113.6) | — | 9,069 (4,113.6) |

| Stream or Component | 10 | 11 | 12 | 13 | 14 | 15 | 16 | 17 |
|---|---|---|---|---|---|---|---|---|
| $H_2$ | — | — | — | — | — | 35 (16) | — | — |
| $N_2$ | — | — | — | — | — | — | — | — |
| $O_2$ | — | — | — | — | — | — | — | — |
| Propylene | — | — | — | — | — | — | — | — |
| Propylene oxide | — | — | — | — | — | — | — | — |
| MBA-PG ether | 290 (132) | 869 (394) | 87 (39.5) | 695 (315) | 87 (39.5) | — | — | — |
| $H_2O_2$ | — | — | — | — | — | — | — | — |
| $H_2O$ | 5,323 (2,414) | 54 (24.5) | — | — | — | — | — | 53 (24) |
| Formic acid | 336 (152) | 3 (1.36) | — | — | — | — | — | 3 (1.36) |
| Acetic Acid | 375 (170) | 4 (1.81) | — | — | — | — | — | 4 (1.81) |
| Ethylbenzene | 39 (17.7) | 386,437 (175,285) | — | 3,489 (1,583) | 933 (423) | — | — | 382,015 (173,279) |
| MBA | 86 (39) | 864,785 (392,259) | 2,119 (961) | 845,274 (383,410) | 3,193 (1,448) | — | 2,643 (1,199) | 17,115 (8,035) |
| Acetophenone | 3 (1.36) | 28,006 (12,703) | 74 (34) | 27,735 (12,580) | 74 (34) | — | 365 (166) | 194 (88) |
| Phenol | 1,279 (580) | 13 (5.9) | — | 3 (1.36) | — | — | — | — |
| EBHP | — | — | — | — | — | — | — | — |
| BAMBE | 372 (169) | 8,698 (3,945) | 8,698 (3,945) | — | 6,711 (3,044) | — | — | — |

Sample 1:

A 100 mL Parr reactor is charged with a 70:23:7 wt. % solution of methanol/water/30 wt. % hydrogen peroxide (40 g) and TS-1 catalyst (0.03 g). The reactor is sealed and charged with propylene (about 20-23 g). The magnetically stirred reaction mixture is heated at 50° C. for 30 minutes at a reactor pressure of about 300 psig (2,170 kPa), then cooled to 10° C. The liquid and gas phases are analyzed by gas chromatography. The results are shown in Table 1.

Sample 2:

A 100 mL Parr reactor is charged with a 70:23:7 wt. % solution of methanol/water/30 wt. % hydrogen peroxide (40 g), 0.5 g of 0.1 M ammonium acetate solution and TS-1 catalyst (0.03 g). The reactor is sealed and charged with propylene (about 21 g). The magnetically stirred reaction mixture is heated at 50° C. for 30 minutes at a reactor pressure of about 300 psig (2,170 kPa), then cooled to 10° C. The liquid and gas phases are analyzed by gas chromatography. The results are shown in Table 1.

Sample 3:

A 100 mL Parr reactor is charged with a 70:23:7 wt. % solution of t-butyl alcohol/water/30 wt. % hydrogen peroxide (40 g) and TS-1 catalyst (0.03 g). The reactor is sealed and charged with propylene (about 25 g). The magnetically stirred reaction mixture is heated at 50° C. for 30 minutes at a reactor pressure of about 300 psig (2,170 kPa), then cooled to 10° C. The liquid and gas phases are analyzed by gas chromatography. The results are shown in Table 1.

Sample 4

A 100 mL Parr reactor is charged with a 70:23:7 wt. % solution of t-butyl alcohol/water/30 wt. % hydrogen peroxide (40 g), 0.5 g of 0.1 M ammonium dihydrogen phosphate solution and TS-1 catalyst (0.03 g). The reactor is sealed and charged with propylene (about 22 g). The magnetically stirred reaction mixture is heated at 50° C. for 30 minutes at a reactor pressure of about 300 psig (2,170 kPa), then cooled to 10° C. The liquid and gas phases are analyzed by gas chromatography. The results are shown in Table 1.

Sample 5

A 100 mL Parr reactor is charged with a 70:23:7 wt. % solution of acetonitrile/water/30 wt. % hydrogen peroxide (40 g), and TS-1 catalyst (0.03 g). The reactor is sealed and charged with propylene (about 22 g). The magnetically stirred reaction mixture is heated at 50° C. for 30 minutes at a reactor pressure of about 300 psig (2,170 kPa), then cooled to 10° C. The liquid and gas phases are analyzed by gas chromatography. Results are shown in table 1.

Sample 6:

A 100 mL Parr reactor is charged with a 70:23:7 wt. % solution of acetonitrile/water/30 wt. % hydrogen peroxide (40 g), 0.5 g of 0.1 M ammonium dihydrogen phosphate solution and TS-1 catalyst (0.03 g). The reactor is sealed and charged with propylene (about 25 g). The magnetically stirred reaction mixture is heated at 50° C. for 30 minutes at a reactor pressure of about 300 psig (2,170 kPa), then cooled to 10° C. The liquid and gas phases are analyzed by gas chromatography. The results are shown in Table 1.

Sample 7:

A 100 mL Parr reactor is charged with a 70:23:7 wt. % solution of t-butyl alcohol/water/30 wt. % hydrogen peroxide (40 g) and TiMWW catalyst (0.03 g). The reactor is sealed and charged with propylene (about 24 g). The magnetically stirred reaction mixture is heated at 50° C. for 30 minutes at a reactor pressure of about 300 psig (2,170 kPa), then cooled to 10° C. The liquid and gas phases are analyzed by gas chromatography. The results are shown in Table 1.

Sample 8:

A 100 mL Parr reactor is charged with a 70:23:7 wt. % solution of t-butyl alcohol/water/30 wt. % hydrogen peroxide (40 g), 0.5 g of 0.1 M ammonium dihydrogen phosphate solution and TiMWW catalyst (0.03 g). The reactor is sealed and charged with propylene (about 24 g). The magnetically stirred reaction mixture is heated at 70° C. for 30 minutes at a reactor pressure of about 300 psig (2,170 kPa), then cooled to 10° C. The liquid and gas phases are analyzed by gas chromatography. The results are shown in Table 1.

Sample 9:

A 100 mL Parr reactor is charged with a 80:12:8 wt. % solution of 1-phenylethyl alcohol/acetophenone/30 wt. % hydrogen peroxide (50 g), and TiMWW catalyst (0.03 g). The reactor is sealed and charged with propylene (about 15 g). The magnetically stirred reaction mixture is heated at 70° C. for 30 minutes at a reactor pressure of about 300 psig (2,170 kPa), then cooled to 10° C. The liquid and gas phases are analyzed by gas chromatography. The results are shown in Table 1.

Sample 10:

A 100 mL Parr reactor is charged with a 80:12:8 wt. % solution of 1-phenylethyl alcohol/acetophenone/30 wt. % hydrogen peroxide (50 g), 0.2 g of 0.1 M ammonium acetate solution and TiMWW catalyst (0.03 g). The reactor is sealed and charged with propylene (about 15 g). The magnetically stirred reaction mixture is heated at 70° C. for 30 minutes at a reactor pressure of about 300 psig (2,170 kPa), then cooled to 10° C. The liquid and gas phases are analyzed by gas chromatography. The results are shown in Table 1.

Sample 11:

A 100 mL Parr reactor is charged with a 80:12:8 wt. % solution of 1-phenylethyl alcohol/acetophenone/30 wt. % hydrogen peroxide (50 g), 0.2 g of 0.1 M ammonium acetate solution and TiMWW catalyst (0.03 g). The reactor is sealed and charged with propylene (about 4.5 g). The magnetically stirred reaction mixture is heated at 70° C. for 30 minutes at a reactor pressure of about 300 psig (2,170 kPa), then cooled to 10° C. The liquid and gas phases are analyzed by gas chromatography. The results are shown in Table 1.

Example 2

Use of TiMWW and Layered TiMWW Catalyst with Buffer and Solvent

TABLE 3

Effects of Catalyst and Buffer on Peroxide Conversion

| Samples | Zeolite Catalyst | Solvent | Buffer | Temp (° C.) | Peroxide conversion (%) |
|---|---|---|---|---|---|
| 12 | TiMWW | t-butyl alcohol/water | — | 70 | 27 |
| 13 | Layered TiMWW-NAW | t-butyl alcohol/water | — | 70 | 99 |
| 14 | Layered TiMWW-AW | t-butyl alcohol/water | — | 70 | 99 |
| 15 | Layered TiMWW-AW | t-butyl alcohol/water | Ammonium Acetate | 70 | 99 |
| 9 | TiMWW | 1-phenylethyl alcohol/ acetophenone | — | 70 | 20.7 |
| 16 | Layered TiMWW-NAW | 1-phenylethyl alcohol/ acetophenone | — | 70 | 99 |
| 17 | Layered TiMWW-AW | 1-phenylethyl alcohol/ acetophenone | — | 70 | 99 |

Preparation of Layered TiMWW-NAW

A sealed 100 mL Parr reactor containing 6.1 g of TiMWW, 15 g of piperidine, and 35 g of deionized water is heated at 155° C. for 3 days. The reaction mixture is then cooled, filtered, washed with de-ionized water (6×200 mL) and dried in a vacuum oven at 130° C. for 16 hrs to yield an off-white solid (5.4 g).

Preparation of Layered TiMWW-AW:

A mixture of the layered TiMWW-NAW catalyst (1.5 g) above in 75 mL of 2 M nitric acid is refluxed at 110° C. After 3 hrs, the reaction mixture is cooled, filtered, washed with de-ionized water (6×200 mL) and dried in a vacuum oven at 130° C. for 16 hrs to yield a white solid (1.2 g).

Sample 12:

A 100 mL Parr reactor is charged with a 70:23:7 wt. % solution of t-butyl alcohol/water/30 wt. % hydrogen peroxide (50 g) and TiMWW catalyst (0.03 g). The reactor is sealed and charged with propylene (about 15 g). The magnetically stirred reaction mixture is heated at 70° C. for 30 minutes at a reactor pressure of about 300 psig (2,170 kPa) and is then cooled to 10° C. The liquid and gas phases are analyzed by gas chromatography. The results are shown in Table 3. In further experiments, the TiMWW/t-butyl alcohol/water conversion of peroxide as described from Sample 12 was observed to be up to 33%.

Sample 13:

A 100 mL Parr reactor is charged with a 70:23:7 wt. % solution of t-butyl alcohol/water/30 wt. % hydrogen peroxide (50 g) and layered TiMWW-NAW catalyst (0.03 g). The reactor is sealed and charged with propylene (about 15 g). The magnetically stirred reaction mixture is heated at 70° C. for 30 minutes at a reactor pressure of about 300 psig (2,170 kPa), then cooled to 10° C. The liquid and gas phases are analyzed by gas chromatography. The results are shown in Table 3.

Sample 14

A 100 mL Parr reactor is charged with a 70:23:7 wt. % solution of t-butyl alcohol/water/30 wt. % hydrogen peroxide (50 g) and layered TiMWW-AW catalyst (0.03 g). The reactor is sealed and charged with propylene (about 15 g). The magnetically stirred reaction mixture is heated at 70° C. for 30 minutes at a reactor pressure of about 300 psig (2,170 kPa), then cooled to 10° C. The liquid and gas phases are analyzed by gas chromatography. The results are shown in Table 3.

Sample 15:

A 100 mL Parr reactor is charged with a 70:23:7 wt. % solution of t-butyl alcohol/water/30 wt. % hydrogen peroxide (50 g), 0.2 g of 0.1M ammonium acetate and layered TiMWW-AW catalyst (0.03 g). The reactor is sealed and charged with propylene (about 15 g). The magnetically stirred reaction mixture is heated at 70° C. for 30 minutes at a reactor pressure of about 300 psig (2,170 kPa), then cooled to 10° C. The liquid and gas phases are analyzed by gas chromatography. The results are shown in Table 3.

Sample 16:

A 100 mL Parr reactor is charged with a 80:12:8 wt. % solution of 1-phenylethyl alcohol/acetophenone/30 wt. % hydrogen peroxide (50 g) and layered Ti-MWW-NAW catalyst (0.03 g). The reactor is sealed and charged with propylene (about 15 g). The magnetically stirred reaction mixture is heated at 70° C. for 30 minutes at a reactor pressure of about 300 psig (2,170 kPa), then cooled to 10° C. The liquid and gas phases are analyzed by gas chromatography. The results are shown in Table 3.

Sample 17:

A 100-mL Parr reactor is charged with a 80:12:8 wt. % solution of 1-phenylethyl alcohol/acetophenone/30 wt. % hydrogen peroxide (50 g) and layered TiMWW-AW catalyst (0.03 g). The reactor is sealed and charged with propylene (about 15 g). The magnetically stirred reaction mixture is heated at 70° C. for 30 minutes at a reactor pressure of about 300 psig (2,170 kPa), then cooled to 10° C. The liquid and gas phases are analyzed by gas chromatography. The results are shown in Table 3.

The TiMWW catalyst has been shown to produce moderate peroxide conversion in t-butyl alcohol and lower peroxide conversion in 1-phenylethyl alcohol (Samples 12 and Samples 9, respectively). The use of a layered TiMWW catalyst as described herein gave increased peroxide conversion for t-butyl alcohol (Samples 13 and 14 as compared to Sample 12) or in 1-phenylethyl alcohol/acetophenone (Sample 16 and 17 as compared to Sample 9). Similarly, the layered TiMWW catalyst when used in conjunction with a buffer also leads to excellent peroxide conversion (e.g., 99% or greater; see Sample 15).

Example 3

Hydrogenation to Remove BAMBE

Sample 18:

A 50 mL Parr reactor containing BAMBE (0.23 g) and 0.2 g palladium on activated carbon (5%) in ethanol (30 g) was pressurized with 10 psig (115 kPa) $H_2$. The reaction mixture was then stirred at ambient temperature for 2 hrs. The reaction was stopped, cooled to 0° C. and depressurized to ambient pressure with nitrogen. The reaction mixture was filtered, with the filtrate analyzed by GC. The results indicated 54% conversion of the BAMBE to products. The molar ratio of the products EB:MBA is 4:1.

Sample 19:

The conditions were the same as the reaction above (Sample 18), but the reaction was charged with 100 psig (790 kPa) $H_2$ instead of 10 psig (170 kPa). With the higher psig of $H_2$, the conversion of BAMBE to product is 100% and molar ratio of EB:MBA is 50:1

Sample 20:

A 50 mL Parr reactor containing BAMBE (0.23 g) and 0.61 g KL7752 (commercially available from Criterion) in ethanol (15 g) was pressurized with 500 psig (3,550 kPa) $H_2$. The reaction mixture was then stirred at 80° C. for 6 hrs. The reaction was stopped, cooled to 0° C. and depressurized to ambient pressure with nitrogen. The reaction mixture was filtered and the filtrate was analyzed by GC. The results indicated 18% conversion of the BAMBE to products. The molar ratio of the products EB:MBA is 1.1:1.

Sample 21:

A 50 mL Parr reactor containing BAMBE (0.22 g), alpha-methylbenzyl alcohol (0.22 g), acetophenone (0.22 g) and 0.2 g palladium on activated carbon (5%) in ethanol (30 g) was pressurized with 100 psig (790 kPa) $H_2$. The reaction mixture was then stirred at ambient temperature for 2 hrs. The reaction was stopped, cooled to 0° C. and depressurized to ambient pressure with nitrogen. The reaction mixture was filtered and the filtrate was analyzed by GC. The results indicated 52% conversion of the BAMBE to products.

Sample 22:

A 50 mL Parr reactor containing BAMBE (0.2 g), alpha-methylbenzyl alcohol (17.46 g) and acetophenone (2.42 g) was pressurized with 100 psig (790 kPa) $H_2$. The reaction mixture was then stirred at 80° C. for 1 hr. The reaction was stopped, cooled to 0° C., and depressurized to ambient pressure with nitrogen. The reaction mixture was filtered and the filtrate was analyzed by GC. The results indicated 12% conversion of the BAMBE to products.

All of the compounds, complexes, and methods disclosed and claimed herein can be made and executed without undue experimentation in light of the present disclosure. While the compounds, complexes, and methods have been described in terms of preferred embodiments, it will be apparent to those of skill in the art that variations may be applied to the compounds, complexes, and methods, as well as in the steps or in the sequence of steps of the method described herein without departing from the concept, spirit, and scope of the appended claims. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the appended claims.

REFERENCES

The following references to the extent that they provide procedural or other details supplementary to those set forth herein, are specifically incorporated herein by reference.

U.S. Pat. No. 6,759,540
U.S. Pat. No. 8,124,555
U.S. Pat. No. 8,440,846
Japanese Publication No. 2011-111431
Anderson, N. G., Practical Process Research & Development—A Guide For Organic Chemists, 2nd ed., Academic Press, New York, 2012.
Lafond, et al., J. of Molecular Catalyst, 182-183:81-88, 2002.
March's Advanced Organic Chemistry: Reactions, Mechanisms, and Structure, 2007.

Wu, et al., "A Novel Titanosilicate with MWW Structure. I. Hydrothermal Synthesis, Elimination of Extraframework Titanium, and Characterizations," J. Phys. Chem. B, 105 (15):2897-2905, 2001.

What is claimed is:

1. A method of preparing propylene oxide comprising:
   (a) oxidizing alpha-methylbenzyl alcohol with air to form a first reaction mixture comprising hydrogen peroxide and acetophenone;
   (b) reacting propylene with the first reaction mixture in the presence of a catalyst to form a second reaction mixture comprising propylene oxide;
   (c) separating the propylene oxide from the second reaction mixture to form a third reaction mixture;
   (d) heating the third reaction mixture to decompose hydrogen peroxide, whereby a fourth reaction mixture is formed;
   (e) hydrogenating the acetophenone in the fourth reaction mixture with hydrogen to form a fifth reaction mixture comprising alpha-methylbenzyl alcohol; and
   (f) separating alpha-methylbenzyl alcohol from the fifth reaction mixture and returning the methyl benzyl alcohol to step (a).

2. The method of claim 1, wherein the molar ratio the alpha-methylbenzyl alcohol to the oxygen of the air of step (a) is from 1:1 to 10:1.

3. The method of claim 1, wherein the oxidizing reaction of step (a) is conducted at a temperature from 100° C. to 160° C.

4. The method of claim 1, wherein the catalyst is a titanium support on zeolite catalyst.

5. The method of claim 4, wherein the titanium support on zeolite catalyst is a TiMWW catalyst or a layered TiMWW catalyst.

6. The method of claim 1, wherein the molar ratio of propylene to hydrogen peroxide in step (b) is from 3:1 to 10:1.

7. The method of claim 1, wherein step (b) is conducted at a temperature from 20° C. to 150° C. and a pressure from 80 psig to 800 psig.

8. The method of claim 1, wherein step (b) further comprises a solvent.

9. The method of claim 8, wherein the solvent is alpha-methylbenzyl alcohol and acetophenone or t-butyl alcohol.

10. The method of claim 1, wherein step (b) comprises a ratio of alpha-methylbenzyl alcohol to acetophenone to hydrogen peroxide to water from 96:1:2.9:0.1 to 44:44:11.7:0.3.

11. The method of claim 1, wherein step (b) further comprises conducting the epoxidation reaction in the presence of a buffer.

12. The method of claim 11, wherein the buffer is ammonium acetate, ammonium phosphate, or ammonium dihydrogen phosphate.

13. The method of claim 1, wherein the separation of step (c) comprises distilling the propylene oxide from the second reaction mixture.

14. The method of claim 1, wherein step (d) is conducted at a temperature from 150° C. to 200° C.

15. The method of claim 1, wherein the molar ratio of the acetophenone to hydrogen in step (e) is from 1:4 to 10:1.

16. The method of claim 1, wherein step (e) is conducted at a temperature from 60° C. to 100° C. and at a pressure from 250 psig to 500 psig.

17. The method of claim 1, wherein the separation of step (f) comprises distilling the alpha-methylbenzyl alcohol from the fifth reaction mixture.

18. The method of claim 1, further comprising washing the fifth reaction mixture with a base.

19. The method of claim 18, where the base is an aqueous solution of sodium hydroxide or potassium hydroxide with a concentration from 0.1 wt. % to 25 wt. %.

20. The method of claim 1, further comprising reacting the fifth reaction mixture after the separation of alpha-methylbenzyl alcohol with hydrogen in the presence of a hydrogenation catalyst forming a sixth reaction mixture and returning at least the methyl benzyl alcohol from the sixth reaction mixture to step (a).

* * * * *

UNITED STATES PATENT AND TRADEMARK OFFICE
CERTIFICATE OF CORRECTION

PATENT NO. : 9,643,943 B2  
APPLICATION NO. : 15/093370  
DATED : May 9, 2017  
INVENTOR(S) : Vu A. Dang et al.

Page 1 of 1

It is certified that error appears in the above-identified patent and that said Letters Patent is hereby corrected as shown below:

In the Specification

Column 1  Line 33  Delete " 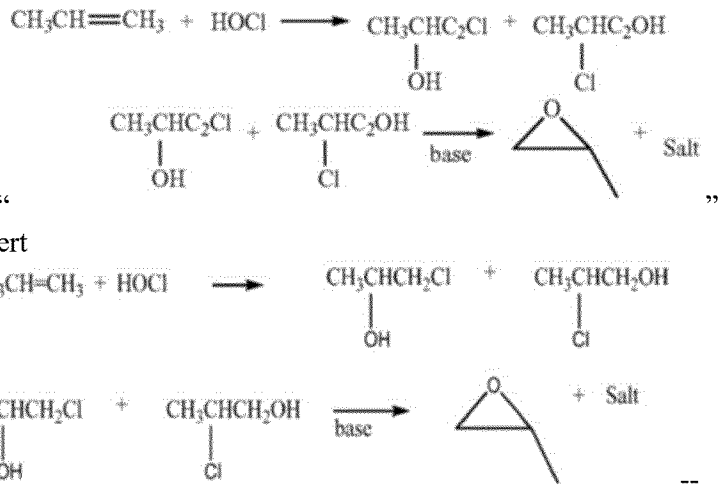 "
and insert

Column 5  Line 59  Delete "Alpha-methylbenxyl" and insert --Alpha-methylbenzyl--
Column 6  Line 1   Delete "teed" and insert --feed--

Signed and Sealed this  
Seventh Day of January, 2020

Andrei Iancu  
*Director of the United States Patent and Trademark Office*